United States Patent [19]
Lederer et al.

[11] Patent Number: 5,690,639
[45] Date of Patent: Nov. 25, 1997

[54] MEDICAL WRENCH

[75] Inventors: Louis Murray Lederer; Gustavo F. Nunez, both of Tucson, Ariz.

[73] Assignee: Very Inventive Physicians, Inc., Tucson, Ariz.

[21] Appl. No.: 730,734

[22] Filed: Oct. 11, 1996

[51] Int. Cl.[6] ............................................. A61B 17/04
[52] U.S. Cl. .......................... 606/104; 81/57.37; 81/125; 81/121.1
[58] Field of Search ................... 606/104; 81/57.37, 81/180.1, 121.1

[56] References Cited

U.S. PATENT DOCUMENTS

| | | | |
|---|---|---|---|
| 2,688,991 | 9/1954 | Doyle | 81/180.1 |
| 4,003,417 | 1/1977 | Cornwell | 81/57.37 |
| 4,030,383 | 6/1977 | Wagner | 81/180.1 |
| 4,809,569 | 3/1989 | Erb | 81/121.1 |
| 5,141,520 | 8/1992 | Goble et al. | 606/104 |
| 5,378,102 | 1/1995 | Mossman | 81/57.37 |
| 5,517,883 | 5/1996 | Goldi et al. | 81/125 |

*Primary Examiner*—Gary Jackson

[57] ABSTRACT

An improved wrench for use in a surgical setting in which a surgical fastener, such as a pin, is supported at a mid-section as well as its base end. The invention uses a tool which has a handle and a mating portion for the surgical pin. This mating portion may be a pong to engage a slot at the pin's base, a hexagonal head to surround the pin's hexagonal shaped base, a semi-circle, or many other such mechanisms well known to those in the art. A sleeve member extends from around the mating portion to extend to a mid-section of the surgical pin to provide sliding support for the surgical pin.

18 Claims, 2 Drawing Sheets

MEDICAL WRENCH

BACKGROUND

This invention relates generally to medical instruments and more particularly to a wrench used to adjust pins and screws applied to a patient.

For a large number of surgical procedures, surgical fasteners must be applied to the patient. These fasteners are typically applied into the patient's bone and provide anchoring for a wide assortment of apparatus including such medical devices as distractors.

Common among these fasteners are surgical pins which are typically driven in manually by the surgeon into the patient's bone. In this procedure, the location for the pin is established and then the pin is rotated using a tool so that the threads of the pin pull the pin into the bone.

While this procedure is commonly done, the task is made more difficult by the surgical environment itself in which there is usually a great deal of blood and other liquids present which make the surgeon's task only more difficult.

Due to the wet environment of the surgical site and the bone's natural curvature, there is always a chance that the pin will slip, thereby impaling another part of the patient.

Further, the current methodology and equipment requires the use and coordination of both of the surgeon's hands. One hand holds and controls the tool while the second hand aligns and supports the surgical pin. This two-handed approach is extremely cumbersome.

It is clear that there is a need for an improved wrench for the application of surgical screws and other such medical fasteners.

SUMMARY OF THE INVENTION

The invention is an improved wrench for use in a surgical setting in which the surgical fastener, such as a pin, is supported at a mid-section as well as at its base end.

In the preferred embodiment, there are three components which are used cooperatively to set surgical pins. The surgical pin, a tool, and a sleeve member.

The pin is any of a variety of well known surgical pins which are adapted to be inserted, through a rotational motion into the bone of the patient. These pins typically have a sharpened first end with screw threads proximate thereto. The other end of the pin includes a connection which permits the pin to be driven by the surgeon via a handle. This connection on one end of the pin is usually a slot but other configurations are also available including, but not limited to, semi-circular, square and hexagonal heads.

The tool has a handle and a mating portion for the surgical pin. Preferably, the tool is manufactured of stainless steel when the tool is to be sterilized and reused. In another embodiment of the invention, the tool is manufactured of hardened plastic and is intended to be a "disposable" after the surgery.

The handle on the tool is shaped to be comfortably accepted by the surgeon's hand so that the tool can be efficiently pressed against the pin.

The mating portion of the tool is selected based upon the particular connection used by the surgical pin. The mating portion, in the preferred embodiment, is a straight extension which is configured to be accepted into the slot on the surgical pin's end.

A variety of other configurations for the mating portion are available and are obvious to those of ordinary skill in the art. These include: a hexagonal head to surround the pin's hexagonal shaped base; a square head to surround the pin's square shaped base; a "+" shaped extension to be inserted into the base of the surgical pin; and, a semi-circular head to engage a pin's semi-circular shaped end.

A sleeve member extends from around the mating portion to extend to a mid-section of the surgical pin to provide sliding support for the surgical pin and hold the pin against gravity. By providing tight tolerance, "wobble" within the pin is minimized.

The sleeve is configured to permit the surgical pin to extend through the sleeve and allow the base member of the surgical pin to make contact and engage the mating portion of the tool. In the preferred embodiment, the distal end of the sleeve, that furthest from the tool, is concave to assist in the insertion of the surgical pin. Further, the concave portion is adapted to encircle the surgical pin in such a way that the pin is restricted from lateral movement while allowing longitudinal movement along the length of the surgical pin.

The internal diameter of the sleeve is such that it prevents the pin from falling. This creates a "one-handed" operation.

In this manner, the surgical pin is held by both the tool (at the base of the pin) and at a mid-section of the pin by the collar. Lateral movement of the pin is all but eliminated; this permits the surgeon to apply pressure against the base of the pin without fear of slippage or skidding of the pin or driver which could puncture the patient's skin.

One embodiment of the invention is a kit for use in a surgical setting. This kit is formed by a tool, a selection of varying sleeves, and a selection of surgical pins. The combination is provided in a sterile packaging and is opened at the surgical site for immediate use.

The invention, together with various embodiments thereof, will be more fully explained by the attached drawings and the following descriptions.

DRAWINGS IN BRIEF

DRAWINGS IN DETAIL

Figure 1A:
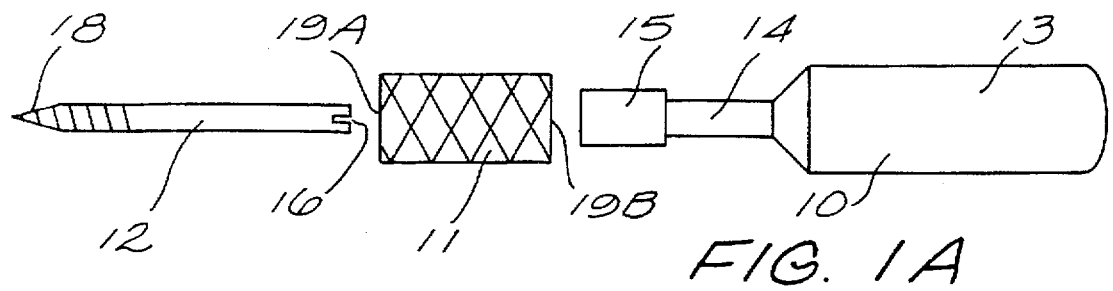
FIGS. 1A and 1B are side views of the preferred embodiment in an unassembled and an assembled state.
Figure 1B:
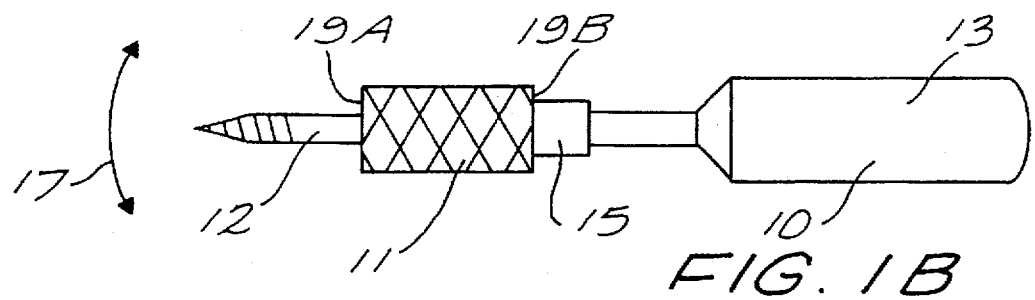

FIGS. 1A and 1B are side views of the preferred embodiment in an unassembled and an assembled state.

The unassembled state, as shown in FIG. 1A, shows the three components: tool 10, sleeve 11, and surgical pin 12.

Surgical pin 12 has one end sharpened and adapted to be inserted into bone of the patient. The other end, in this embodiment, is slotted 16 so that rotational force can be applied to pin 12.

Tool 10 has a handle portion 13, shank 14, and collar 15. Located within collar 15 is a connection member (not shown in this figure) which is adapted to engage slot 16 so that rotation of handle 13 by the surgeon forces pin 12 to rotate as well.

Sleeve 11 has one end 19B configured to engage collar 15; distal end 19A is shaped to accept pin 12.

In some embodiments of the invention, sleeve 11 is made part of tool 10. In the preferred embodiment, sleeve 11 is removable allowing a variety of sleeves to be used with a single tool; these various sleeves have differing passage ways diameters to address varying sized pins.

The assembled state, shown in FIG. 1B, illustrates how pin 12 is inserted through sleeve 11 to engage tool 10. Collar 15 is secured to end 19B. Sleeve 11 has an opening extending the entire length of sleeve 11, but, distal end 19A is configured to snugly fit around pin 12 so that lateral motion, as illustrated by arrow 17, is minimized.

Figure 2:
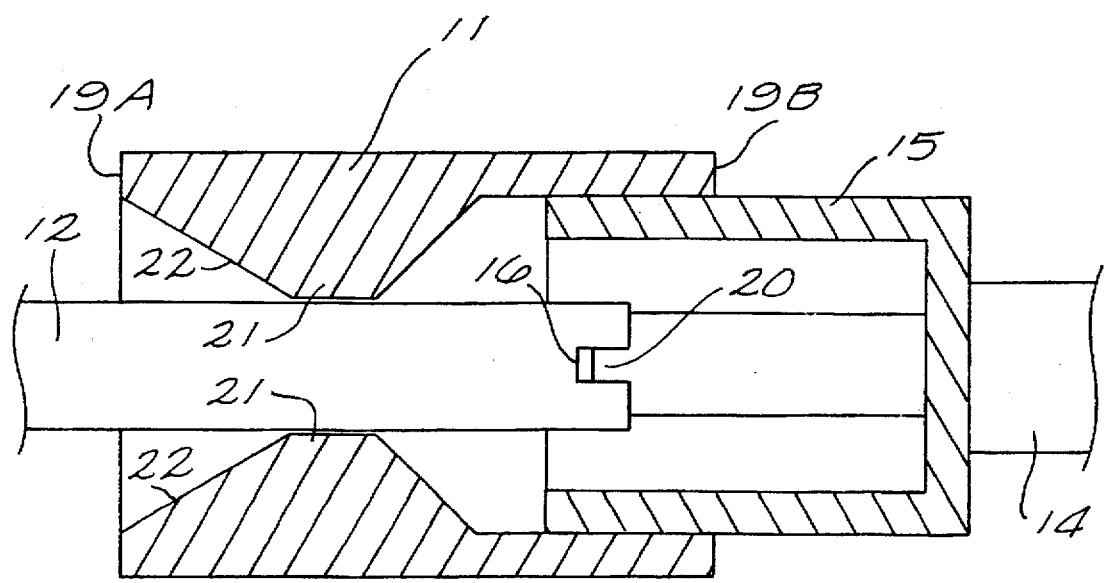
FIG. 2 is a cutaway view of the preferred embodiment illustrating the clasping mechanism of the present invention for a slotted screw.

FIG. 2 is a cutaway view of the preferred embodiment illustrating the clasping mechanism of the present invention for a slotted screw.

As discussed in relationship to FIGS. 1A and 1B, sleeve 11 in engaged with collar 15 at end 19B. Within collar 15 is connecting mechanism 20 which engages slot 16 of surgical pin 12.

Pin 12 passes through sleeve 11 by being inserted into distal end 19A. Concave recess 22 assists in aligning pin 12 between shoulders 21. Shoulders 21 provide a slidable support for a mid-section of surgical pin 12 to minimize lateral motion. The diameter between shoulders 21 is chosen with precision tolerance to both provide support for pin 12 and also to prevent pin 12 from dropping.

Pressure and rotational forces applied via shank 14, are easily communicated to surgical pin 12. Due to shoulders 21, the forces applied along shank 14 are properly restrained to longitudinal forces since surgical pin 12 is restrained from "wobbling" during its insertion into the patient's bone.

Figure 3:
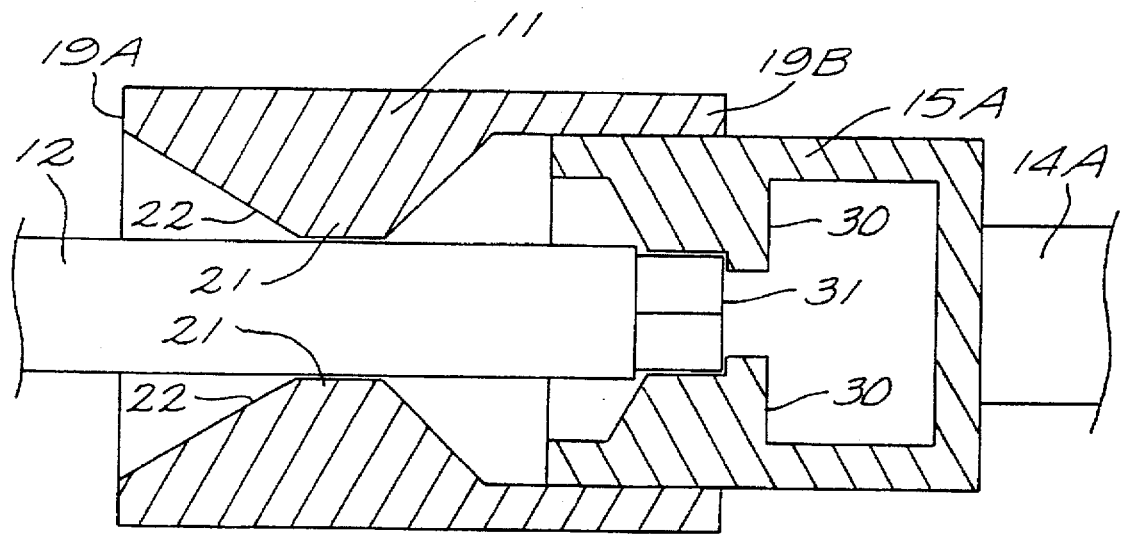
FIG. 3 is a cutaway view of an alternative embodiment of the invention illustrating the clasping mechanism of the present invention for a hexagonal head.

FIG. 3 is a cutaway view of an alternative embodiment of the invention illustrating the clasping mechanism of the present invention for a hexagonal head.

In this embodiment, sleeve 11 in engaged with collar 15A at end 19B. Within collar 15A is head 30 which engages the hexagonal base member 31 of pin 12. The use of head 30 together with hexagonal base member 31 provides for an extremely secure connection between pin 12 and collar 15A.

As discussed with relationship to FIG. 2, pin 12 passes through sleeve 11 by being inserted into end 19A. Concave recess 22 assists in aligning pin 12 between shoulders 21. Shoulders 21 provide a slidable support for a mid-section of surgical pin 12 to minimize lateral motion.

Figure 4:
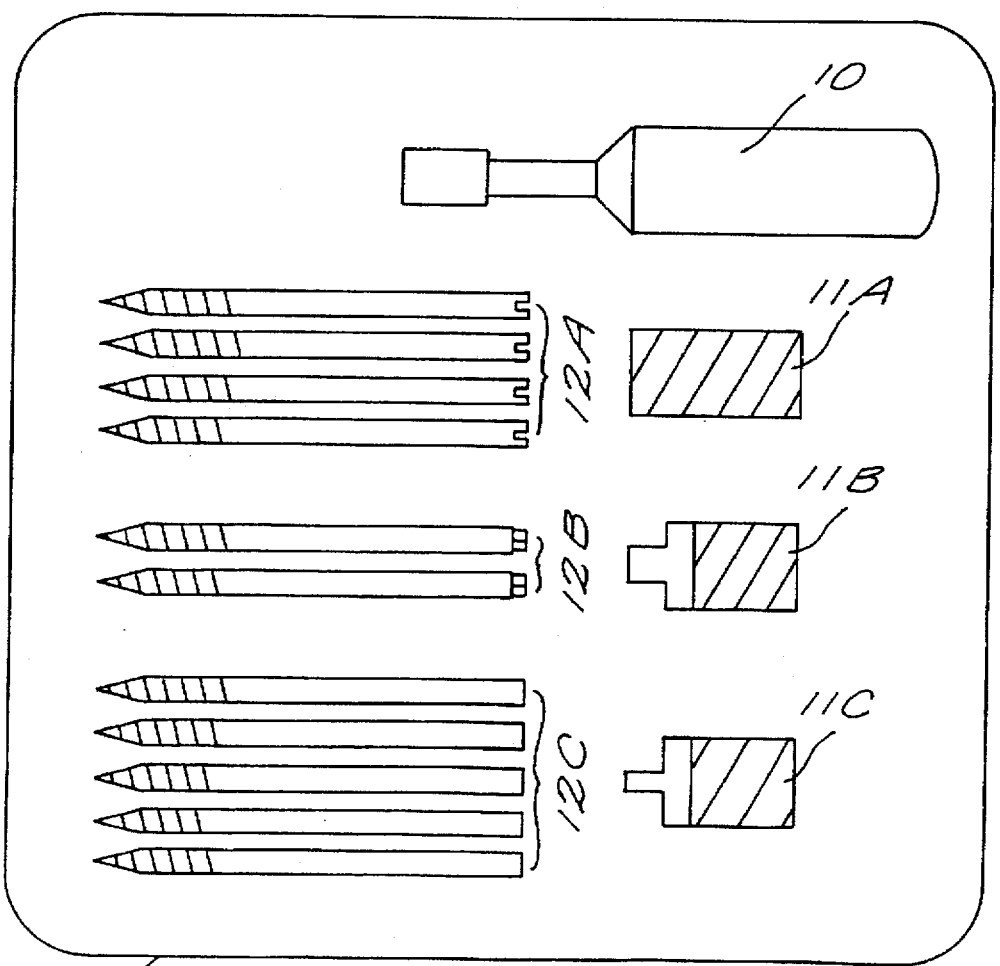
FIG. 4 is a layout of the preferred embodiment of the kit for the present invention.

FIG. 4 is a layout of the preferred embodiment of the kit for the present invention.

In many applications, there is a need for a sterile, prepackaged collection for the surgical site. This embodiment of the invention provides a tool 10 which is collected with a variety of sleeves 11A, 11B, and 11C, as well as a variety of differing size diameter surgical pins 12A, 12B, and 12C. The entire combination is contained within package 40 which maintains the items in a sterile condition.

When the surgeon is ready to use the materials, package 40 is opened. Tool 10 is extracted and the proper size surgical pin is removed together with the associated sleeve.

It is clear that the present invention creates a highly improved wrench mechanism for the application of surgical fasteners.

What is claimed is:

1. A combination comprising:
   a) a fixation pin having a substantially circular cross section, a first end of said fixation pin having a slot therein and a second end of said fixation pin being adapted to be screwed into a bone of a patient; and,
   b) a tool having,
      1) a grip member on a first end thereof, a second end of said tool adapted to engage the slot of said fixation pin, and,
      2) a sleeve member secured to said second end of said tool, a first end of said sleeve member adapted to fit over the first end of the fixation pin such that said second end of said tool is engagable with said slot of said fixation pin and said first end of said sleeve slideably engages a mid-section of said fixation pin.

2. The combination according to claim 1 wherein said tool includes a collar member encircling said second end thereof and wherein said sleeve member engages said collar member.

3. The combination according to claim 2 wherein said collar member has a cross section and wherein said sleeve member has an opening adapted to compliment said cross section.

4. The combination according to claim 3 wherein said collar member is substantially circular and wherein the opening of said sleeve member is substantially circular.

5. The combination according to claim 1 wherein said sleeve member is disengageable from said tool.

6. The combination according to claim 1 wherein the first end of said sleeve member is concave.

7. A medical combination comprising:
   a) a tool having a grip member on a first end thereof, a second end configured to engage a fastening member which is adapted to be rotated; and,
   b) a sleeve member securable to said second end of said tool, a first end of said sleeve member adapted to fit over a second end of said tool such that said second end of said tool is engageable with said fastening member and said first end of said sleeve slideably engages a mid-section of said fastening member.

8. The medical combination according to claim 7 wherein said tool includes a collar member encircling said second end thereof and wherein said sleeve member engages said collar member.

9. The medical combination according to claim 8 wherein said collar member has a regular cross section and wherein said sleeve member has an opening adapted to compliment said regular cross section.

10. The medical combination according to claim 9 wherein said collar member and the opening in said sleeve member are substantially circular.

11. The medical combination according to claim 9 wherein said sleeve member is disengageable from said tool.

12. The medical combination according to claim 7 wherein the first end of said sleeve member is concave.

13. A medical kit comprising:
   a) at least two fixation pins, a first end of each of said fixation pins adapted for attachment to a tool, and a second end of each of said fixation pins being adapted to be screwed into a bone of a patient;
   b) a tool having a grip member on a first end thereof, a Second end adapted to be engagable with the first end of said fixation pin; and,
   c) at least two sleeve members, each of said sleeve members individually securable to the second end of said tool, a first end of said sleeve members adapted to fit over the first end of a selected one of the fixation pins such that said second end of said tool is engageable with said fixation pin and wherein said first end of said sleeve slideably engages a mid-section of said selected one of said fixation pins.

14. The medical kit according to claim 13 wherein said tool includes a collar member encircling said second end thereof and wherein each of said sleeve members are individually engagable with said collar member.

15. The medical kit according to claim 14 wherein said collar member has a regular cross section and wherein each of said sleeve members have an opening adapted to compliment said regular cross section.

16. The medical kit according to claim 15 wherein said collar member is substantially circular and wherein said sleeve member has an opening adapted to compliment said collar member.

17. The medical kit according to claim 13 wherein the first end of each of said sleeve members is concave and wherein each of said sleeve members has a channel therethrough having a diameter unique from the other sleeve members.

18. The medical kit according to claim 13 further including a packaging containing said fixation pins, said tool, and said sleeve members, and wherein an interior portion of said packaging is substantially sterile.

\* \* \* \* \*